(12) United States Patent
Middlesworth

(10) Patent No.: US 10,882,294 B2
(45) Date of Patent: Jan. 5, 2021

(54) ELASTIC NON-WOVEN LAMINATION METHOD AND APPARATUS

(71) Applicant: Berry Global, Inc., Evansville, IN (US)

(72) Inventor: Jeffrey A. Middlesworth, Wauconda, IL (US)

(73) Assignee: Berry Global, Inc., Evansville, IN (US)

( * ) Notice: Subject to any disclaimer, the term of this patent is extended or adjusted under 35 U.S.C. 154(b) by 0 days.

(21) Appl. No.: 16/430,660

(22) Filed: Jun. 4, 2019

(65) Prior Publication Data

US 2019/0283389 A1  Sep. 19, 2019

Related U.S. Application Data

(63) Continuation of application No. 15/979,726, filed on May 15, 2018, now Pat. No. 10,350,870.

(Continued)

(51) Int. Cl.
*B29C 65/00* (2006.01)
*B32B 37/14* (2006.01)
(Continued)

(52) U.S. Cl.
CPC ...... *B32B 37/144* (2013.01); *A61F 13/15699* (2013.01); *A61F 13/15723* (2013.01); *A61F 13/15764* (2013.01); *B29C 65/08* (2013.01); *B29C 65/086* (2013.01); *B29C 65/48* (2013.01); *B29C 66/02241* (2013.01); *B29C 66/1122* (2013.01); *B29C 66/344* (2013.01); *B29C 66/45* (2013.01); *B29C 66/47* (2013.01); *B29C 66/4722* (2013.01); *B29C 66/7294* (2013.01); *B29C 66/7392* (2013.01); *B29C 66/81433* (2013.01); *B29C 66/83411* (2013.01); *B29C 66/83413* (2013.01); *B32B 5/022* (2013.01); *B32B 5/26* (2013.01); *B32B 37/025* (2013.01); *B32B 37/06* (2013.01); *B32B 37/12* (2013.01); *B32B 37/1284* (2013.01); *B32B 37/203* (2013.01); *B32B 37/223* (2013.01); *B32B 38/0004* (2013.01); *B32B 38/0012* (2013.01); *B32B 38/10* (2013.01); *B65H 23/1888* (2013.01); *B65H 27/00* (2013.01); *B65H 35/04* (2013.01); *B65H 37/04* (2013.01);
(Continued)

(58) Field of Classification Search
CPC ....... B29C 65/08; B29C 65/086; B29C 65/48; B29C 66/02241; B29C 66/344; B29C 66/45; B29C 66/7294
USPC ...... 156/73.1, 73.4, 229, 250, 252, 437, 510
See application file for complete search history.

(56) References Cited

U.S. PATENT DOCUMENTS

| 4,606,964 A | 8/1986 | Wideman |
| 4,655,760 A | 4/1987 | Morman |

(Continued)

OTHER PUBLICATIONS

International (PCT) Search Report and Written Opinion for PCT/US0218/032714 dated Jul. 20, 2018, BP-518 PCT II (5723-275749), 8 pages.

(Continued)

*Primary Examiner* — Mark A Osele
*Assistant Examiner* — Nickolas R Harm
(74) *Attorney, Agent, or Firm* — Barnes & Thornburg LLP

(57) ABSTRACT

A lamination system includes a film supply, a non-woven material supply, and a laminator. The laminator causes a film from the film supply to be laminated to a sheet from the non-woven material supply to establish a laminated sheet.

20 Claims, 12 Drawing Sheets

Related U.S. Application Data

(60) Provisional application No. 62/507,278, filed on May 17, 2017.

(51) Int. Cl.

| | | |
|---|---|---|
| *B32B 38/00* | (2006.01) | |
| *B32B 37/06* | (2006.01) | |
| *B32B 37/12* | (2006.01) | |
| *B32B 5/02* | (2006.01) | |
| *B29C 65/08* | (2006.01) | |
| *B29C 65/48* | (2006.01) | |
| *B32B 5/26* | (2006.01) | |
| *B32B 37/22* | (2006.01) | |
| *B32B 37/20* | (2006.01) | |
| *A61F 13/15* | (2006.01) | |
| *B65H 23/188* | (2006.01) | |
| *B65H 37/04* | (2006.01) | |
| *B65H 35/04* | (2006.01) | |
| *B32B 38/10* | (2006.01) | |
| *B32B 37/00* | (2006.01) | |
| *B65H 27/00* | (2006.01) | |
| *B65H 39/14* | (2006.01) | |
| *B29L 31/48* | (2006.01) | |

(52) U.S. Cl.
CPC ...... *B65H 39/14* (2013.01); *A61F 2013/1591* (2013.01); *A61F 2013/15869* (2013.01); *A61F 2013/15934* (2013.01); *B29C 66/71* (2013.01); *B29C 2793/0081* (2013.01); *B29K 2995/0046* (2013.01); *B29L 2031/4878* (2013.01); *B32B 2038/0028* (2013.01); *B32B 2250/20* (2013.01); *B32B 2262/02* (2013.01); *B32B 2305/28* (2013.01); *B32B 2307/51* (2013.01); *B32B 2310/028* (2013.01); *B32B 2555/02* (2013.01); *B65H 2301/5124* (2013.01); *B65H 2404/12* (2013.01); *B65H 2404/132* (2013.01); *B65H 2404/154* (2013.01); *B65H 2404/56* (2013.01)

(56) References Cited

U.S. PATENT DOCUMENTS

| | | | |
|---|---|---|---|
| 4,720,415 A | 1/1988 | Vander Wielen | |
| 4,747,846 A | 5/1988 | Boland | |
| 4,795,510 A | 1/1989 | Wittrock | |
| 4,925,520 A | 5/1990 | Beaudoin | |
| 4,995,928 A * | 2/1991 | Sabee | A61F 13/15593 |
| | | | 156/164 |
| 5,167,897 A | 12/1992 | Weber | |
| 5,171,388 A | 12/1992 | Hoffman | |
| 5,235,515 A | 8/1993 | Ungpiyakul | |
| 5,259,902 A | 11/1993 | Muckenfuhs | |
| 5,383,988 A | 1/1995 | Herrmann | |
| 5,407,507 A | 4/1995 | Ball | |
| 5,413,849 A | 5/1995 | Austin | |
| 5,464,401 A | 11/1995 | Hasse | |
| 5,545,285 A | 8/1996 | Johnson | |
| 5,556,504 A | 9/1996 | Rajala | |
| 5,569,234 A | 10/1996 | Buell | |
| 5,580,411 A | 12/1996 | Nease | |
| 5,591,298 A | 1/1997 | Goodman | |
| 5,595,618 A * | 1/1997 | Fries | A61F 13/15756 |
| | | | 156/164 |
| 5,626,571 A | 5/1997 | Young | |
| 5,643,396 A | 7/1997 | Rajala | |
| 5,660,657 A | 8/1997 | Rajala | |
| 5,681,302 A | 10/1997 | Melbye | |
| 5,685,874 A | 11/1997 | Buell | |
| 5,705,013 A | 1/1998 | Nease | |
| 5,769,838 A | 6/1998 | Buell | |
| 5,885,686 A | 3/1999 | Cederblad | |
| 5,985,193 A | 11/1999 | Harrington | |
| 6,022,430 A * | 2/2000 | Blenke | A61F 13/15601 |
| | | | 156/73.1 |
| 6,139,004 A | 10/2000 | Couillard | |
| 6,227,541 B1 | 5/2001 | Couillard | |
| 6,319,347 B1 | 11/2001 | Rajala | |
| 6,342,565 B1 | 1/2002 | Cheng | |
| 6,391,420 B1 | 5/2002 | Cederblad | |
| 6,440,246 B1 | 8/2002 | Vogt | |
| 6,458,726 B1 | 10/2002 | Harrington | |
| 6,475,325 B1 | 11/2002 | Parrish | |
| 6,494,244 B2 | 12/2002 | Parrish | |
| 6,513,221 B2 | 2/2003 | Vogt | |
| 6,531,015 B1 | 3/2003 | Gardner | |
| 6,634,269 B2 | 10/2003 | Eckstein | |
| 6,649,010 B2 | 11/2003 | Parrish | |
| 6,720,279 B2 * | 4/2004 | Cree | A61F 13/5146 |
| | | | 442/394 |
| 6,773,810 B2 | 8/2004 | Sen | |
| 6,811,871 B2 | 11/2004 | Sen | |
| 6,821,370 B2 | 11/2004 | Tomsovic | |
| 6,835,264 B2 | 12/2004 | Sayovitz | |
| 6,855,223 B2 | 2/2005 | Johnson | |
| 6,878,647 B1 | 4/2005 | Rezai | |
| 6,881,375 B2 | 4/2005 | Topolkaraev | |
| 6,896,843 B2 | 5/2005 | Topolkaraev | |
| 6,899,780 B2 | 5/2005 | Rajala | |
| 6,905,565 B2 | 6/2005 | Shimoe | |
| 6,957,160 B2 | 10/2005 | Miller | |
| 6,994,763 B2 | 2/2006 | Austin | |
| 7,008,888 B2 | 3/2006 | Bansal | |
| 7,056,411 B2 | 6/2006 | Desai | |
| 7,238,634 B2 | 7/2007 | Bansal | |
| 7,252,730 B2 | 8/2007 | Hoffman | |
| 7,300,895 B2 | 11/2007 | Kobayashi | |
| 7,329,245 B2 | 2/2008 | Torigoshi | |
| 7,347,846 B2 | 3/2008 | Hermansson | |
| 7,361,246 B2 | 4/2008 | Chang | |
| 7,387,148 B2 | 6/2008 | Vogt | |
| 7,405,171 B2 | 7/2008 | Tsujiyama | |
| 7,449,015 B2 | 11/2008 | Otsubo | |
| 7,530,972 B2 | 5/2009 | Ando | |
| 7,533,709 B2 | 5/2009 | Meyer | |
| 7,540,862 B2 | 6/2009 | Olsson | |
| 7,700,504 B2 | 4/2010 | Tsujiyama | |
| 7,740,727 B2 | 6/2010 | Chang | |
| 7,819,853 B2 | 10/2010 | Desai | |
| 7,938,921 B2 | 5/2011 | Ng | |
| 8,007,623 B2 | 8/2011 | Andrews | |
| 8,016,972 B2 | 9/2011 | Andrews | |
| 8,057,456 B2 | 11/2011 | Shirai | |
| 8,168,024 B2 | 5/2012 | Chang | |
| 8,172,977 B2 | 5/2012 | McCabe | |
| 8,182,627 B2 | 5/2012 | Eckstein | |
| 8,202,390 B2 | 6/2012 | Malowaniec | |
| 8,261,802 B2 | 9/2012 | Aono | |
| 8,333,748 B2 | 12/2012 | Desai | |
| 8,449,515 B2 | 5/2013 | Saito | |
| 8,460,495 B2 | 6/2013 | McCabe | |
| 8,474,502 B2 | 7/2013 | Chang | |
| 8,480,830 B2 | 7/2013 | Chang | |
| 8,523,834 B2 | 9/2013 | Desai | |
| 8,529,536 B2 | 9/2013 | Tsang | |
| 8,673,098 B2 | 3/2014 | McCabe | |
| 8,685,190 B2 | 4/2014 | Chang | |
| 8,697,937 B2 | 4/2014 | Roe | |
| 8,697,938 B2 | 4/2014 | Roe | |
| 8,974,890 B2 * | 3/2015 | Mitsuno | D04H 3/14 |
| | | | 28/116 |
| 9,028,461 B2 | 5/2015 | Kobayashi | |
| 9,066,834 B2 | 6/2015 | Desai | |
| 9,089,453 B2 | 7/2015 | McCabe | |
| 9,095,472 B2 | 8/2015 | Wade | |
| 9,168,720 B2 | 10/2015 | Westwood | |
| 9,205,003 B2 | 12/2015 | Tsang | |
| 9,220,637 B2 | 12/2015 | Roe | |
| 9,289,332 B2 | 3/2016 | Wade | |
| 9,327,477 B2 | 5/2016 | Muslet | |

(56) References Cited

U.S. PATENT DOCUMENTS

| | | | |
|---|---|---|---|
| 9,398,985 B2 | 7/2016 | Langdon | |
| 9,404,215 B2 | 8/2016 | Desai | |
| 9,433,538 B2 | 9/2016 | Pagel | |
| 2002/0164465 A1* | 11/2002 | Curro | A47L 1/15 428/198 |
| 2006/0003656 A1 | 1/2006 | Morman | |
| 2006/0162843 A1* | 7/2006 | Baldauf | B32B 3/22 156/73.1 |
| 2011/0094657 A1* | 4/2011 | McCabe | A61F 13/15593 156/163 |
| 2013/0098545 A1* | 4/2013 | Schroeder | B32B 37/144 156/265 |
| 2015/0313774 A1 | 11/2015 | Homoelle | |
| 2018/0333943 A1* | 11/2018 | Middlesworth | B29C 66/47 |

OTHER PUBLICATIONS

Office Action dated Dec. 14, 2018 for U.S. Appl. No. 15/979,726 (pp. 1-8).

\* cited by examiner

ELASTIC NON-WOVEN LAMINATION METHOD AND APPARATUS

PRIORITY CLAIM

This application is a continuation of U.S. application Ser. No. 15/979,726, filed May 15, 2018, which claims priority under 35 U.S.C. § 119(e) to U.S. Provisional Application Ser. No. 62/507,278, filed May 17, 2017, which is expressly incorporated by reference herein.

BACKGROUND

The present disclosure relates to a lamination system, and particularly to a system for laminating an elastic material to a backing material. More particularly, the present disclosure relates to a system for laminating an elastic non-woven web to a non-woven backing web.

SUMMARY

According to the present disclosure, a lamination system includes a stretcher unit and a laminator. The stretcher unit elongates an elastic non-woven material to form an internal retraction force therein. The laminator bonds the elastic non-woven material to a non-woven backing web.

In illustrative embodiments, the elastic non-woven material is separated into strips prior to elongation. The strips pass between stretcher rolls so that a leading edge of the strip is pulled away from a trailing edge of the strip to elongate the strip. Each stretcher roll includes a plurality of spaced apart fingers configured to at least partially pierce the elastic non-woven material. Each finger is curved and arranged to face a direction of rotation of the stretcher roll to which the finger is attached.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which.

Figure 1:
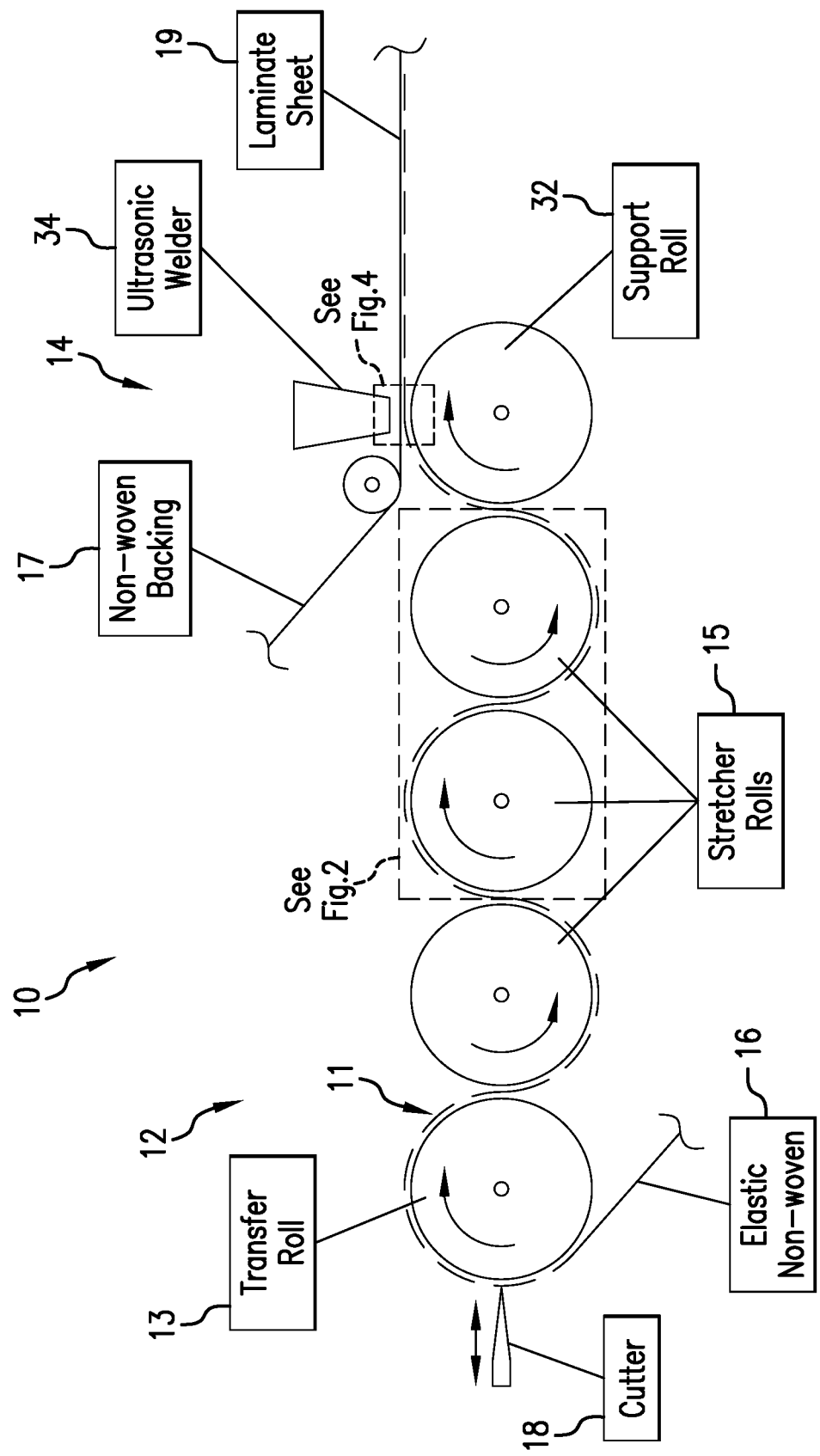
FIG. 1 is a side elevation view of an embodiment of a lamination system in accordance with the present disclosure showing that an elastic non-woven material is sectioned into elongated strips that are secured to a non-woven backing web to form a laminate sheet and suggesting that the elastic non-woven material is stretched and applied to the non-woven backing web in a stretched state.
Figure 4:
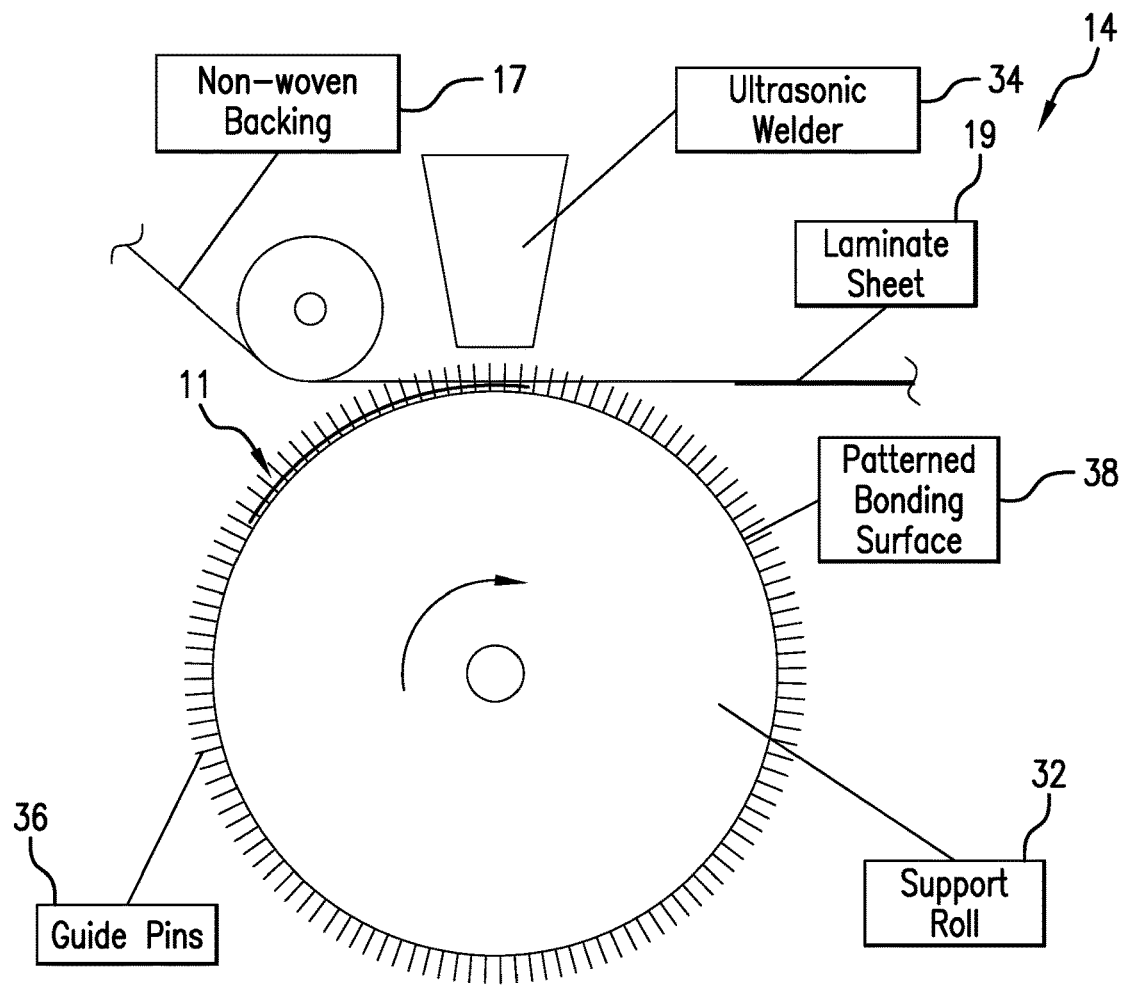
FIG. 4 is a side elevation view of a laminator of the lamination system of FIG. 1 showing that the laminator includes a support roll for supporting and guiding the strips of elastic non-woven material along the non-woven backing web and an ultrasonic welder for bonding the elastic non-woven strips to the non-woven backing web to form the laminate sheet.
Figure 5:
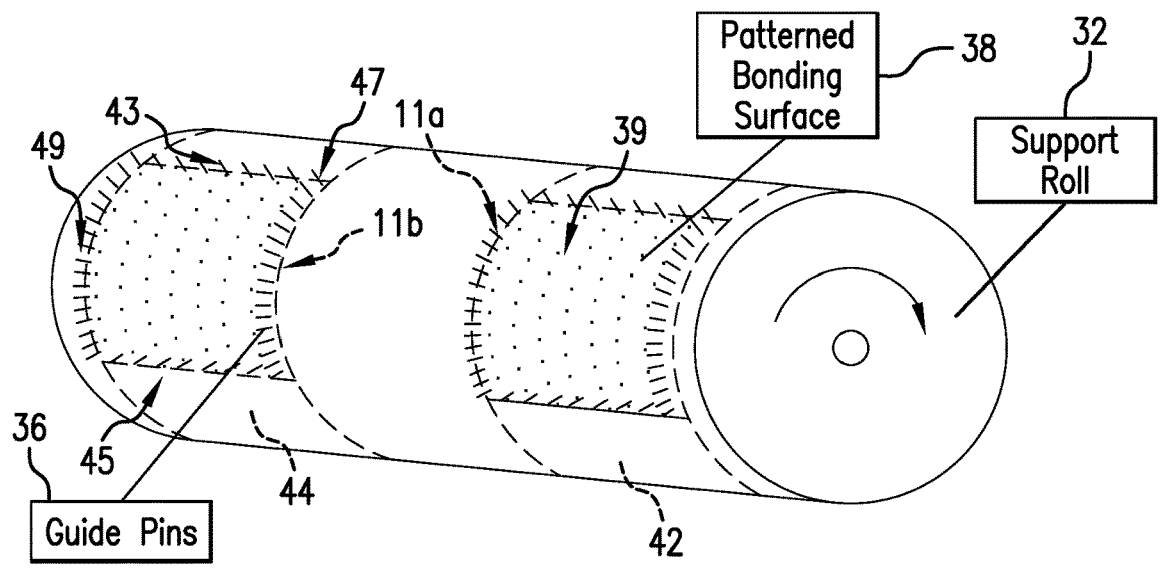
Figure 6:
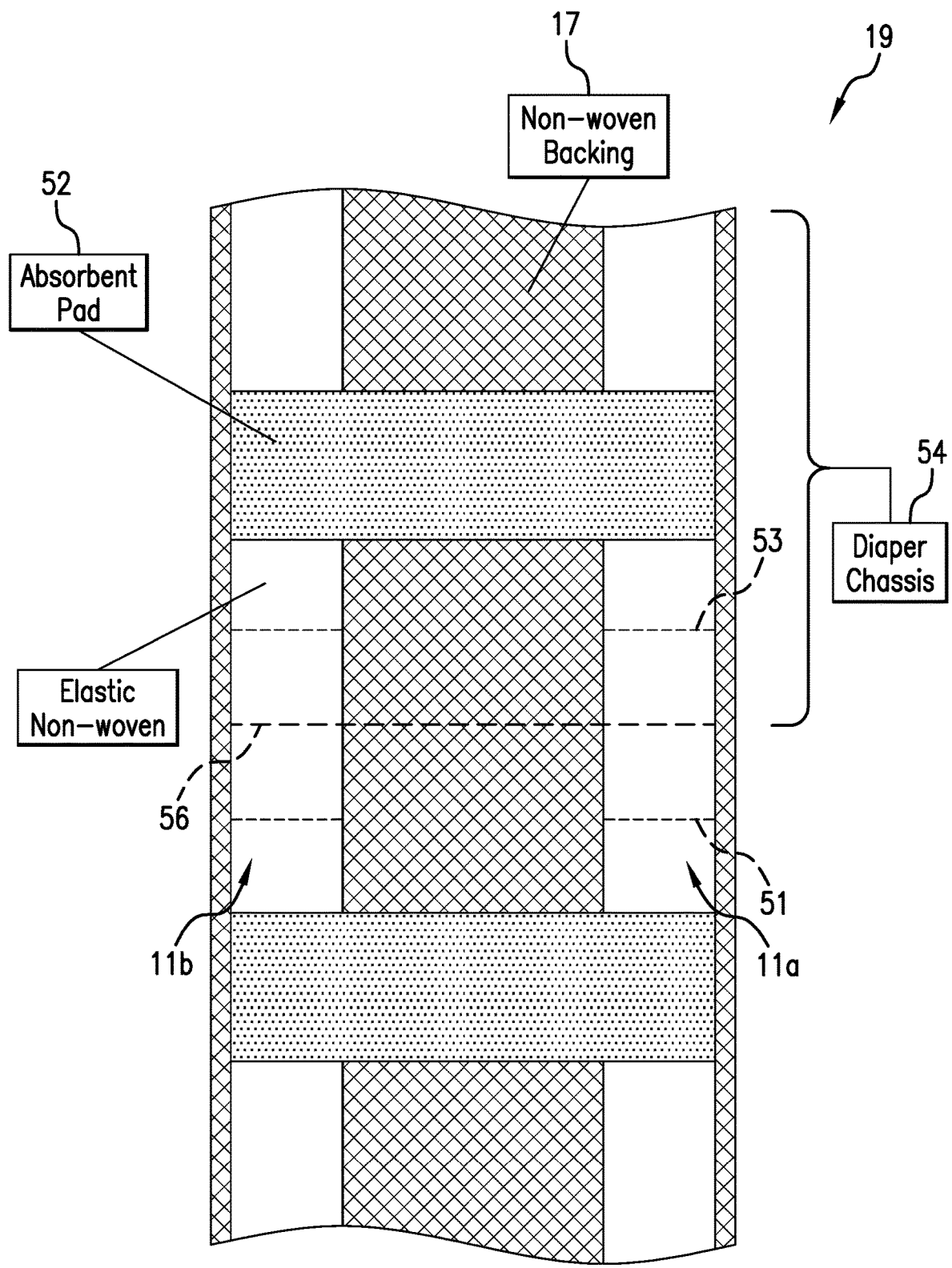
Figure 7:
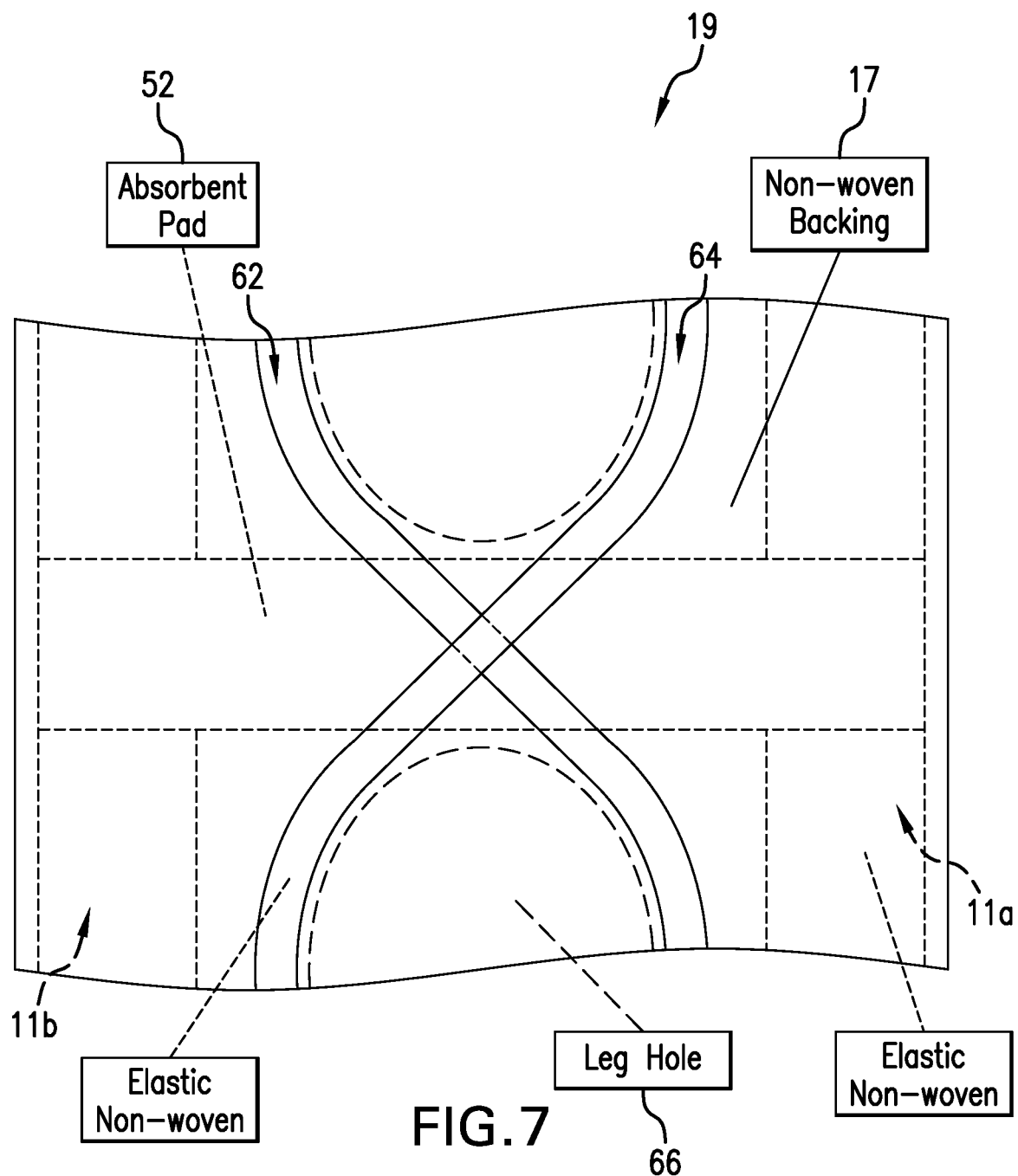
Figure 8:
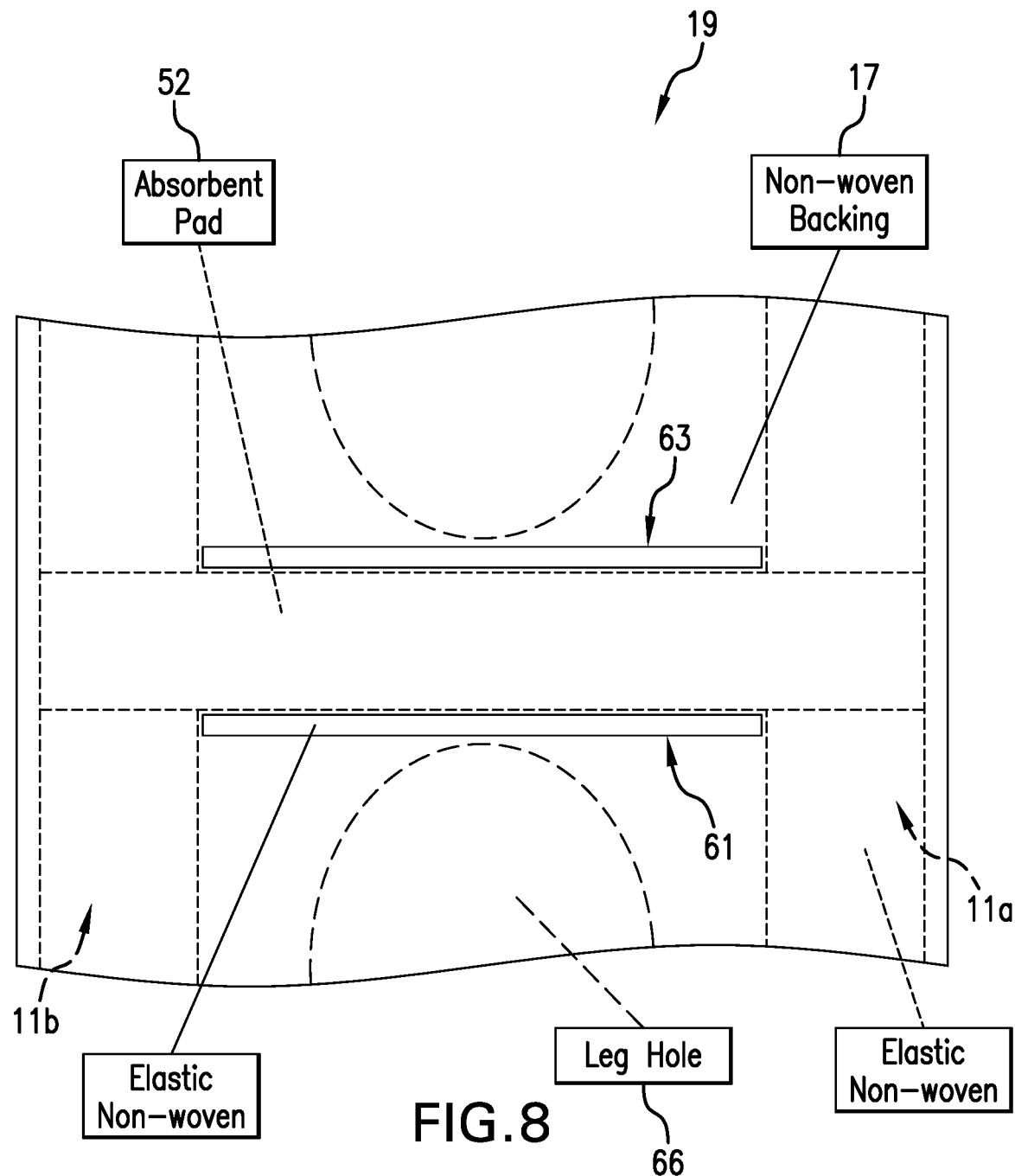
Figure 9:
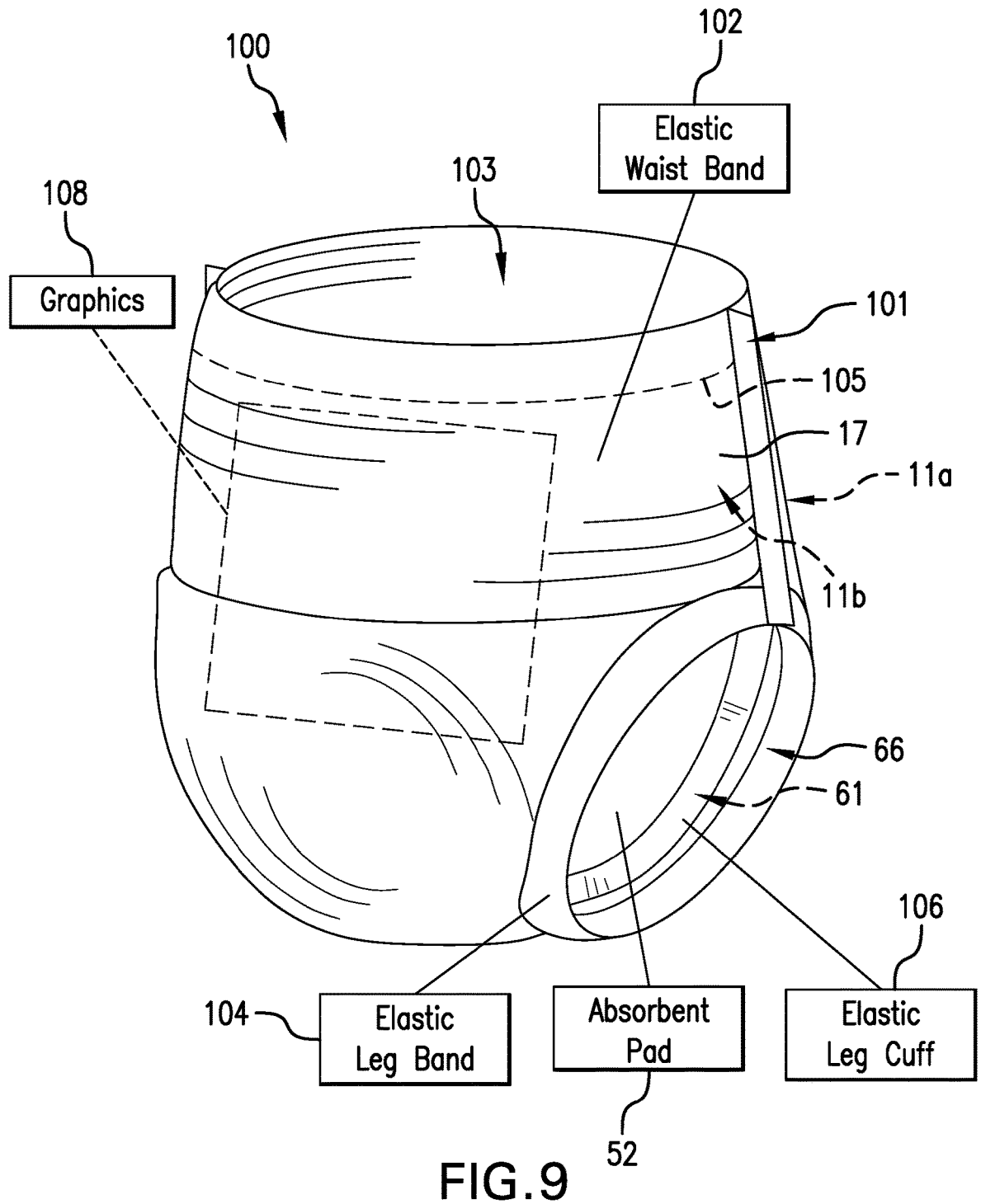
Figure 10:
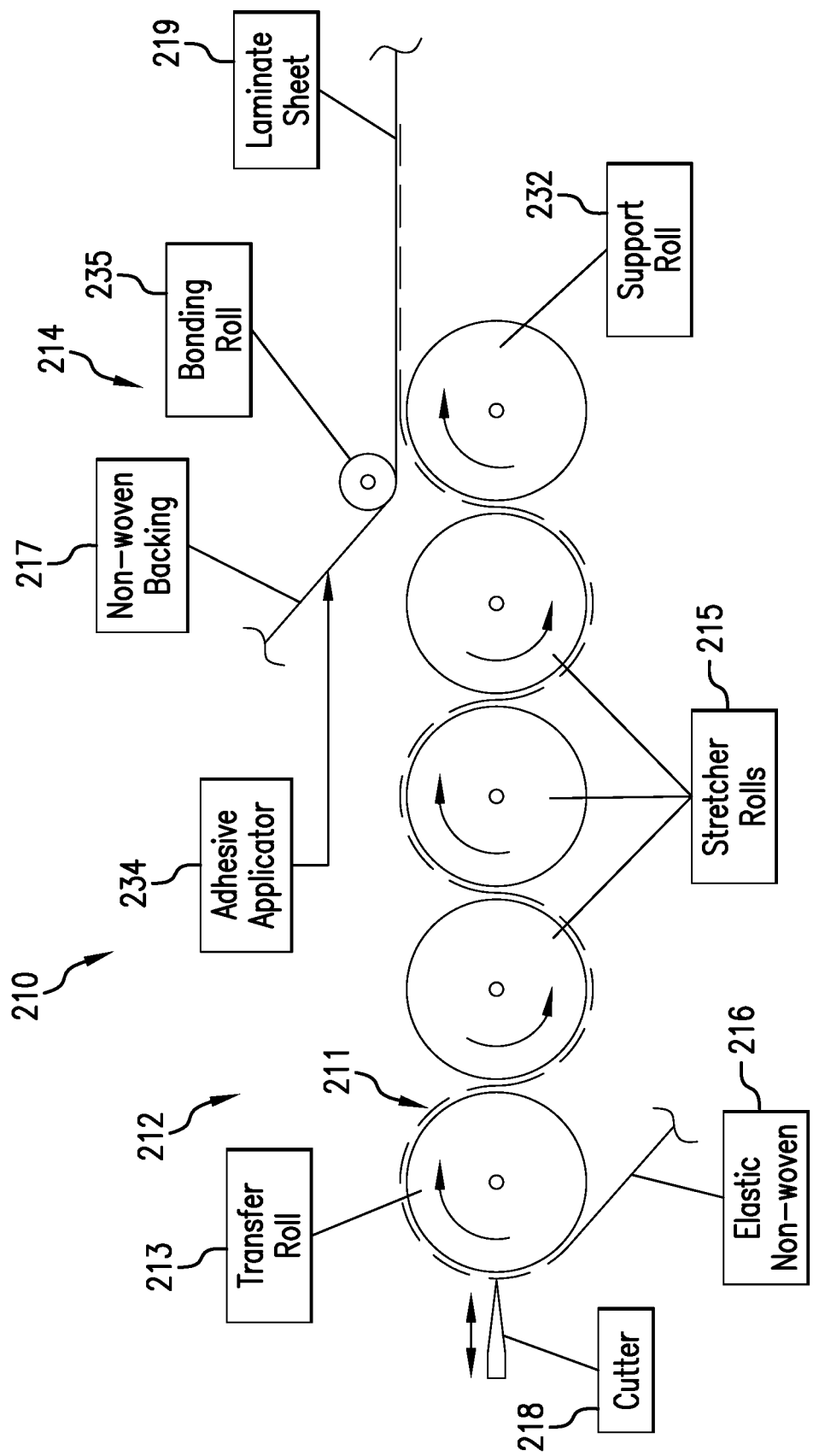
Figure 11:
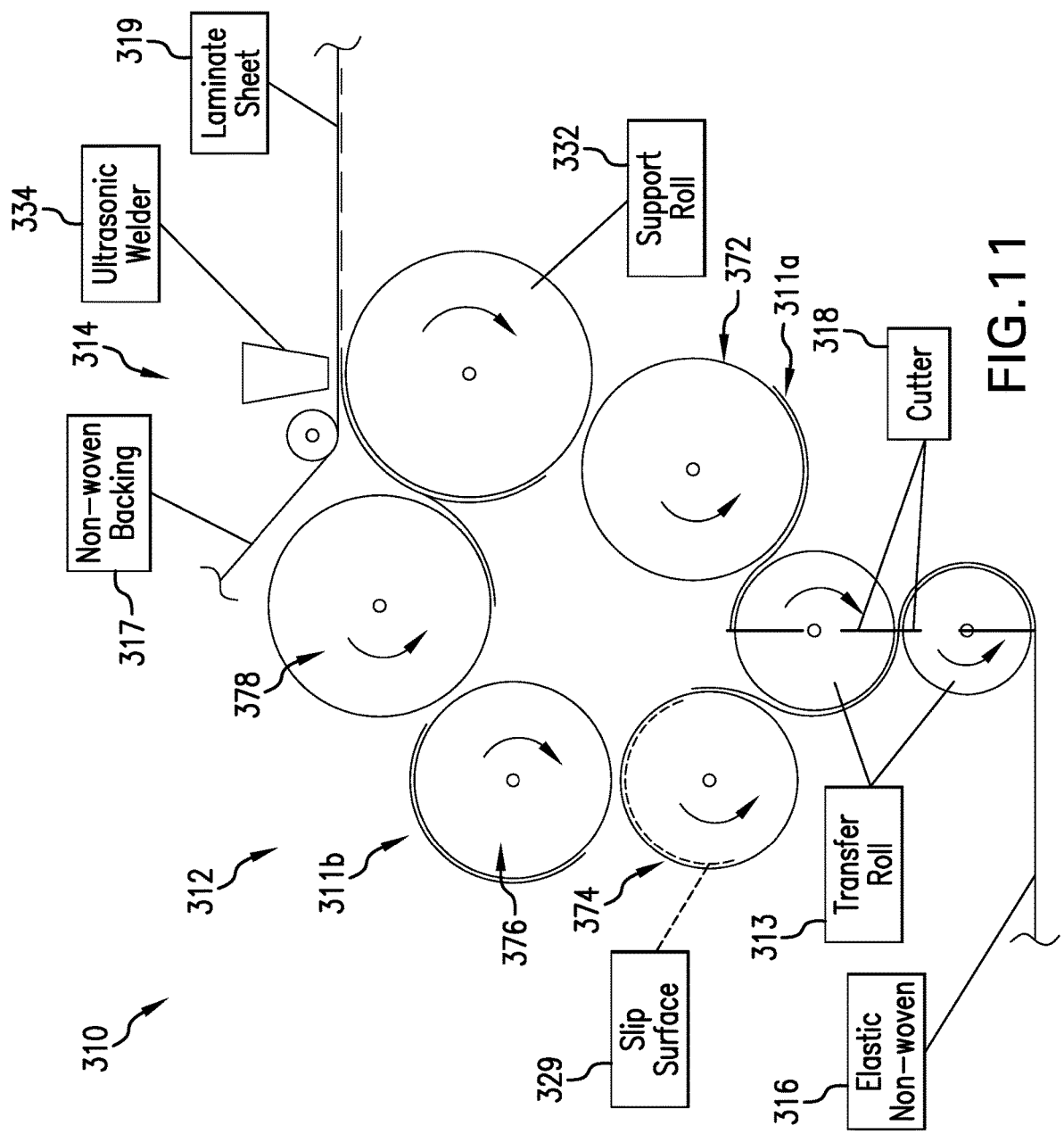
Figure 12:
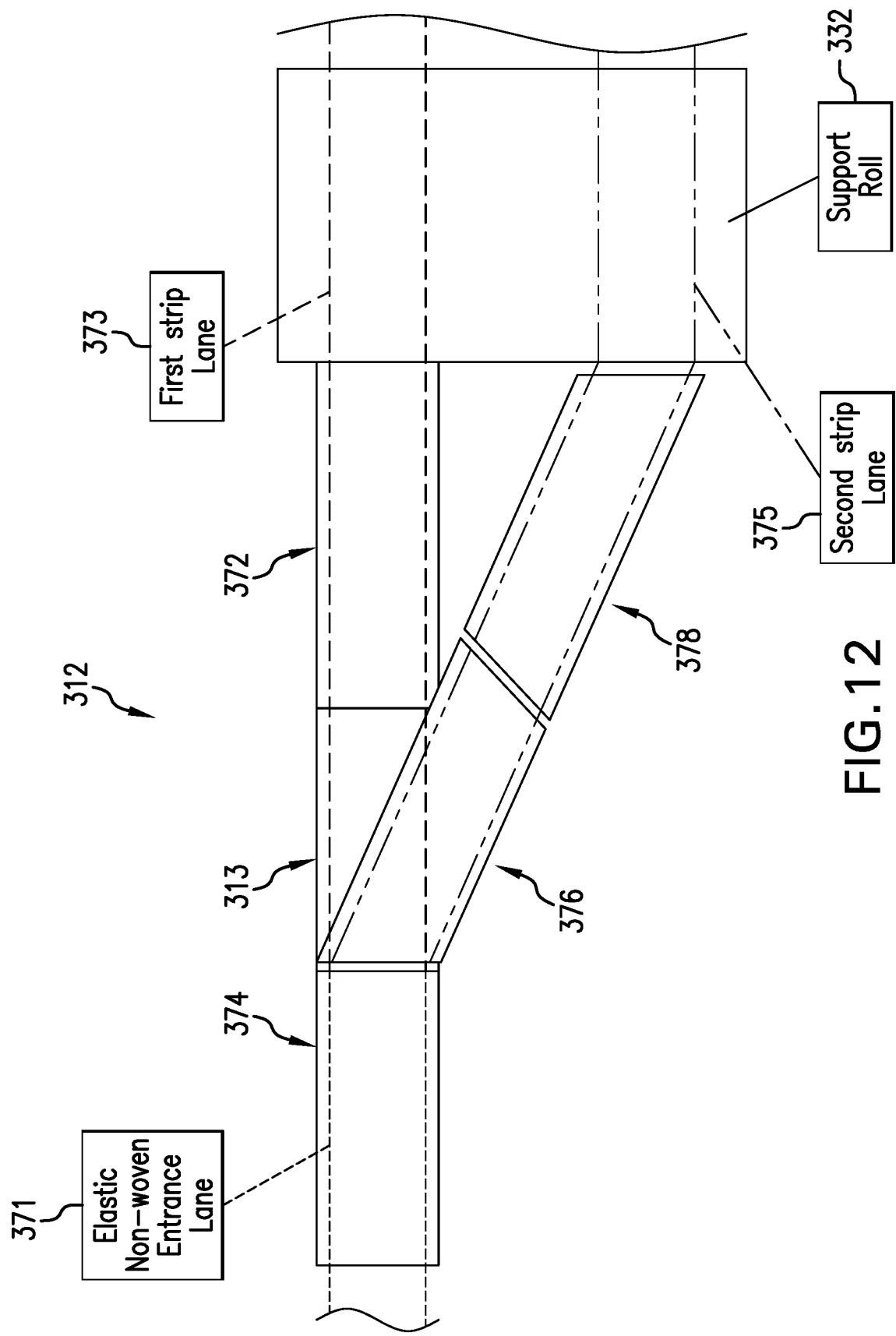
Figure 13:
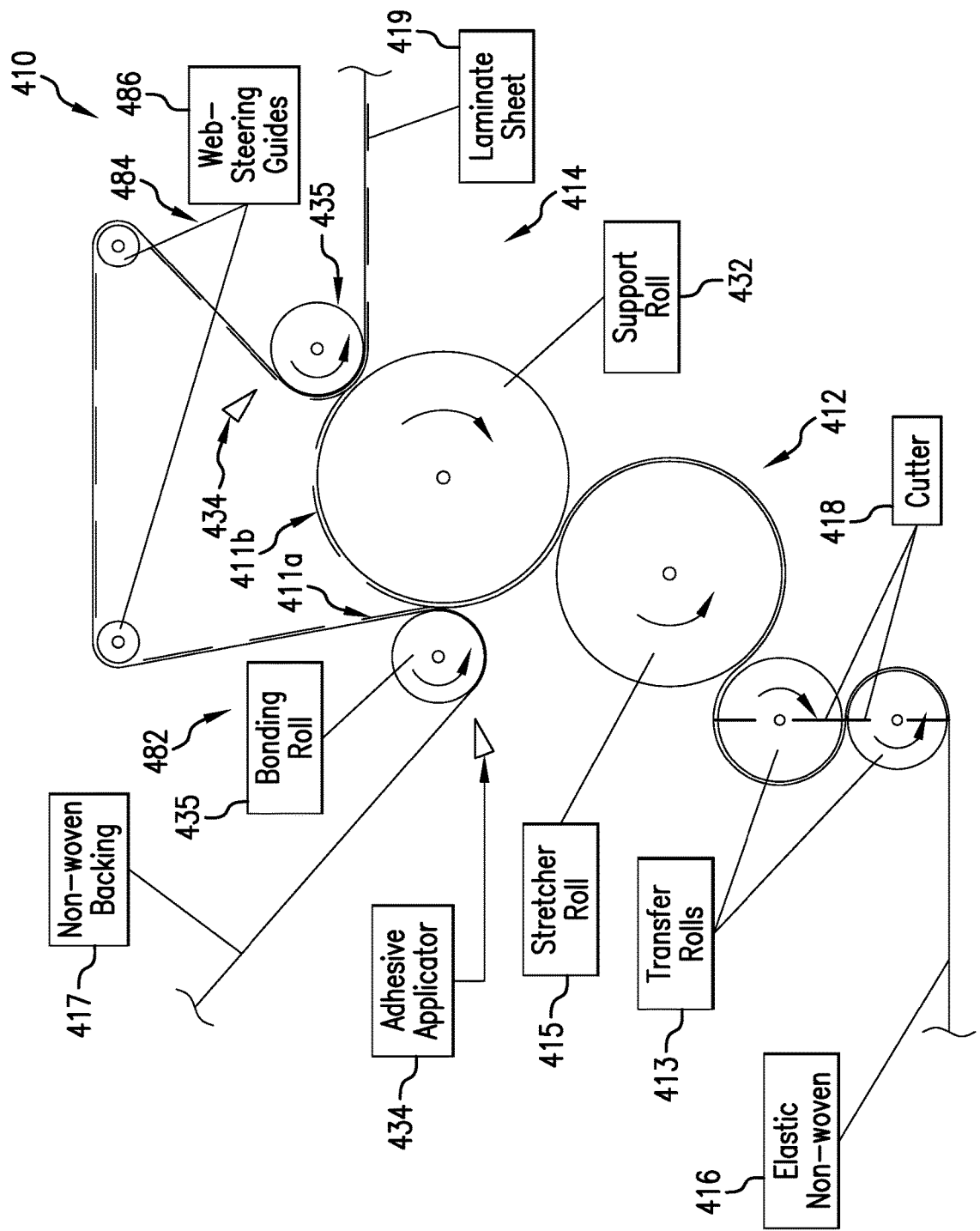
Figure 14:
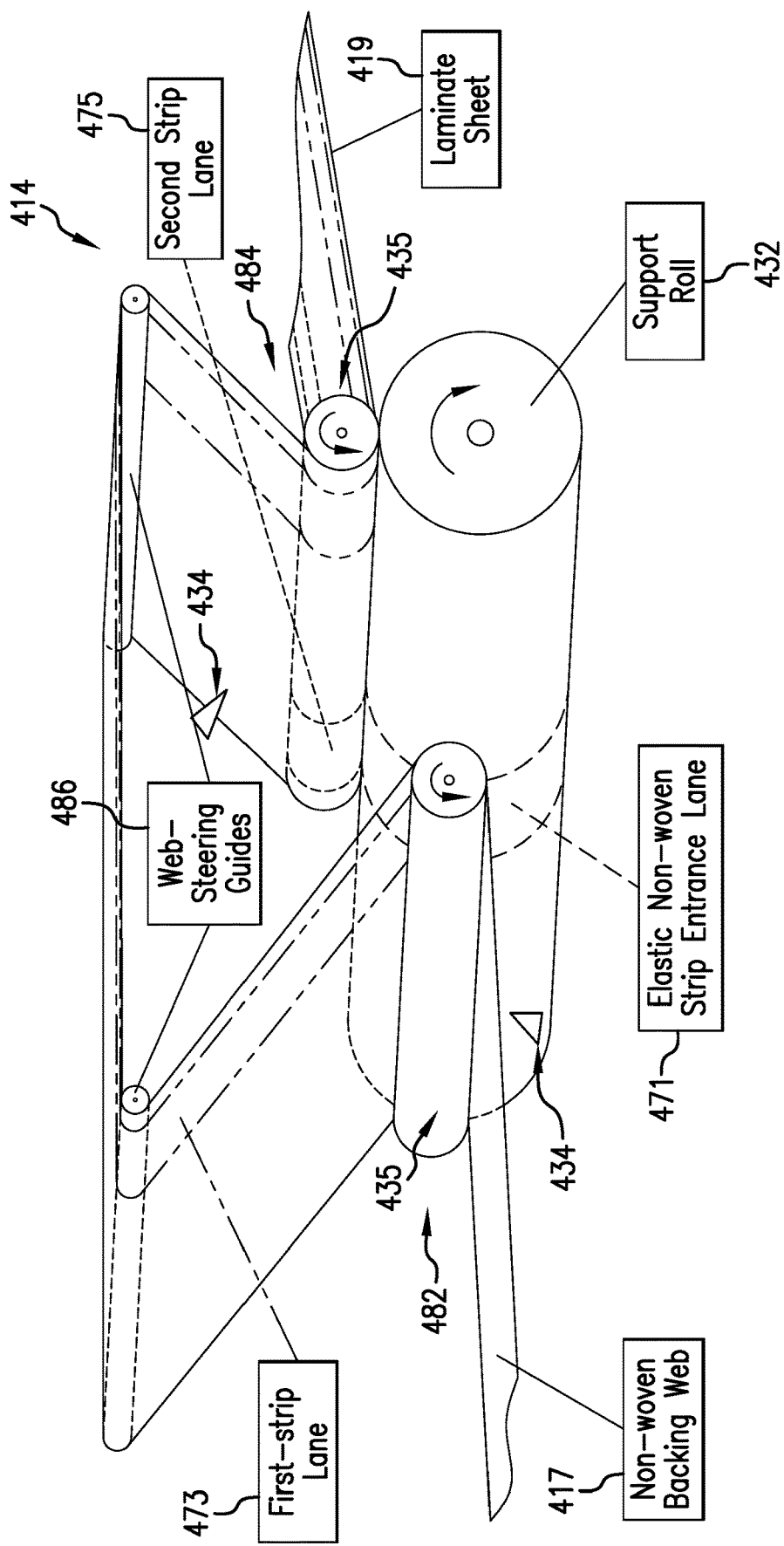

FIG. 5 is a perspective view of the support roll of FIG. 4 showing that the support roll includes guide pins for engaging the elastic non-woven strips to hold the strips in the stretched state and a patterned bonding surface having features to direct energy from the ultrasonic welder for binding of the elastic non-woven strips to the non-woven backing web and suggesting that the guide pins are arranged in lanes to guide multiple strips of elastic non-woven material along the non-woven backing web;

FIG. 6 is a bottom plan view of an embodiment of a laminate sheet produced by the lamination system of FIG. 1 in accordance with the present disclosure showing that the laminate sheet includes the elastic non-woven strips bonded alongside edges of the non-woven backing web and an absorbent pad bonded to the non-woven backing web and extending across the backing web and suggesting that laminate sheet is formed continuously and sectioned into separate diaper chassis used to form diapers as suggested in FIG. 9;

FIG. 7 is a bottom plan view of another embodiment of a laminate sheet produced by the lamination system of FIG. 1 in accordance with the present disclosure showing that elastic non-woven ribbons are applied in a sinusoidal pattern and bonded to a non-woven backing web and suggesting that the elastic non-woven ribbons extend around leg holes of a diaper chassis to provide an elastic leg band of a formed diaper as suggested in FIG. 9;

FIG. 8 is a bottom plan view of another embodiment of a laminate sheet produced by the lamination system of FIG. 1 in accordance with the present disclosure showing that elastic non-woven ribbons are applied along leading and trailing edges of an absorbent pad and bonded to a non-woven backing web and suggesting that the elastic non-woven ribbons provide an elastic leg cuff of a formed diaper as suggested in FIG. 9;

FIG. 9 is a perspective view of a diaper in accordance with the present disclosure showing that the diaper includes an elastic waistband, an elastic leg band, and an elastic leg cuff and suggesting that the elastic waistband, elastic leg band, and elastic leg cuff are formed using an elastic non-woven material;

FIG. 10 is a side elevation view of another embodiment of a lamination system in accordance with the present disclosure showing that an elastic non-woven material is sectioned into elongated strips that are secured to a non-woven backing web to form a laminate sheet and suggesting that the elastic non-woven material is stretched and applied to the non-woven backing web in a stretched state using an adhesive;

FIG. 11 is a side elevation view of another embodiment of a lamination system in accordance with the present disclosure showing that an elastic non-woven material is sectioned into elongated strips that are secured to a non-woven backing web to form a laminate sheet and suggesting that the strips are diverted along separate paths that align the strips for bonding with the non-woven backing web;

FIG. 12 is a top plan view of the lamination system of FIG. 10 showing that stretcher rolls are arranged to divert an incoming stream of elastic non-woven material along separate lanes after being sectioned into strips;

FIG. 13 is a side elevation view of another embodiment of a lamination system in accordance with the present disclosure showing that an elastic non-woven material is sectioned into elongated strips that are secured to a non-woven backing web to form a laminate sheet and suggesting that the non-woven backing web is diverted to align the strips of elastic non-woven along separate paths for bonding with the non-woven backing web; and FIG. 14 is a perspective view of the lamination system of FIG. 13 showing bond rolls offset from one another relative to an entrance lane of the strips of elastic non-woven and suggesting that the non-woven backing web is shifted between the bonding rolls relative to the entrance lane using web-steering guides to align the strips along separate lanes for bonding with the backing web.

DETAILED DESCRIPTION

A lamination system 10 in accordance with the present disclosure is shown in FIG. 1. Lamination system 10 includes a stretcher unit 12 and a laminator 14. A web of elastic non-woven material 16 passes through a cutter 18 of stretcher unit 12 to divide elastic non-woven 16 into strips 11. Strips 11 are carried by a transfer roll 13 of stretcher unit 12 to stretcher rolls 15. Strips 11 pass between stretcher rolls 15 to elongate strips 11 and form an internal retraction force based on the elastic properties of elastic non-woven material 16. The elongated strips 11 pass through laminator 14 to bond with a non-woven backing web 17 to form a laminate sheet 19. Strips 11 are spaced apart from one another in laminate sheet 19 and impart elastic qualities to laminate sheet 19 where bonded to non-woven backing web 17.

Figure 2:
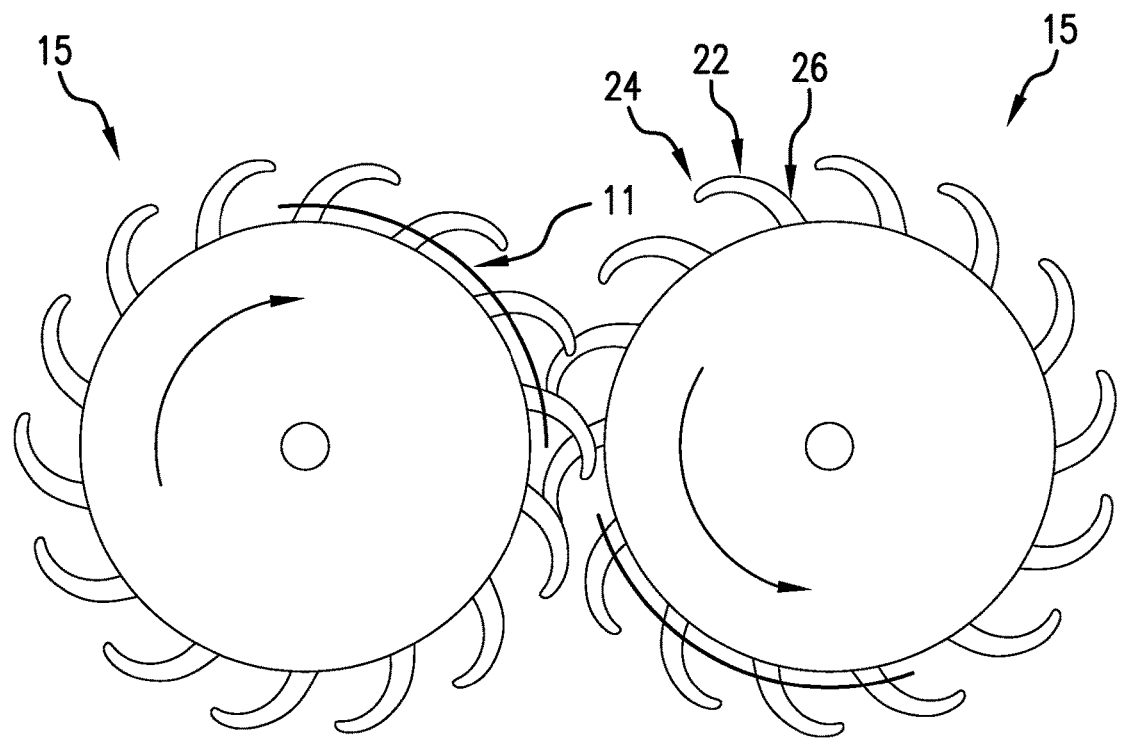
FIG. 2 is a side elevation view of stretcher rolls of the lamination system of FIG. 1 showing adjacent stretcher rolls have opposingly directed fingers that engage with the elastic non-woven and suggesting that subsequent stretcher rolls rotate at increased speeds to pull the elastic non-woven strips from the fingers of the previous roll and further stretch the strips.

Each stretcher roll 15 includes a plurality of curved fingers 22 as suggested in FIG. 2. Adjacent stretcher rolls 15 are counter-rotating compared to one another, and fingers 22 are arranged to curve outwardly in the direction of rotation of the stretcher roll 15 that finger 22 is attached to. Each finger 22 includes a tip 24 and a base 26 for securing fingers 22 to stretcher rolls 15. Tips 24 are configured to pierce at least a portion of strips 11 to pull strips 11 toward stretcher roll 15. Subsequent stretcher rolls 15 in stretcher unit 12 have a faster surface speed than previous stretcher rolls 15 so that a leading edge of each strip 11 is pulled away from a trailing edge of strip 11 as strip 11 passes between stretcher rolls 15 to elongate strip 11. In some embodiments, subsequent stretcher rolls 15 have a larger diameter than previous stretcher rolls 15 and rotate at similar speeds. Fingers 22 of a first stretcher roll 15 in stretcher unit 12 pull strips 11 off of transfer roll 13 as suggested in FIG. 1 (though fingers 22 are not shown in FIG. 1). In some embodiments, particularly for non-porous webs such as an elastic film, transfer roll 13 uses vacuum pressure or electrostatic cling to hold strips on transfer roll 13.

Figure 3:
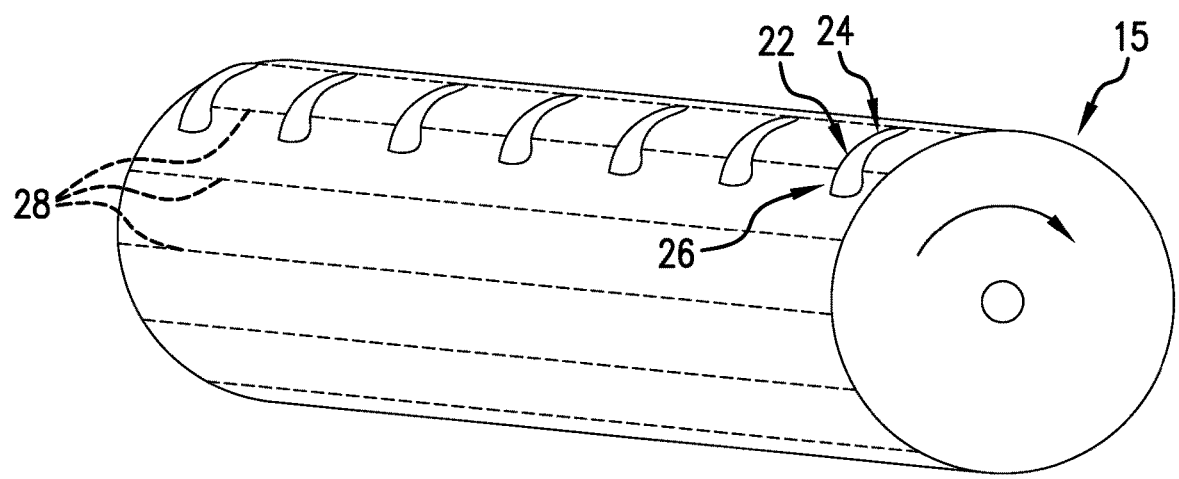
FIG. 3 is a perspective view of one of the stretcher rolls of FIG. 2 showing that the stretcher roll includes a plurality of fingers arranged in a row along a width of the stretcher roll.

Each strip 11 moves toward base 26 of fingers 22 to block retraction of strips 11 as suggested in FIG. 2. In the illustrative embodiment, each finger extends radially outward from stretcher rolls 15 at base 26 and curve toward the direction of rotation of stretcher roll 15 at tip 24. The curved profile and orientation of fingers 22 blocks retraction of strips 11 while allowing subsequent stretcher rolls 15 to pull strips 11 off of previous stretcher rolls 15. A plurality of fingers 22 are arranged along a width of each stretcher roll 15 in a plurality of rows as suggested by phantom lines 28 in FIG. 3. While only one row of fingers 22 is shown in FIG. 3, each phantom line 28 would have an associated row of fingers placed along each phantom line.

In the illustrative embodiment, laminator 14 includes a support roll 32 and an ultrasonic welder 34 as shown in FIG. 4. Support roll 32 includes guide pins 36 and a patterned bonding surface 38. Guide pins 36 pull strips 11 off of a last stretcher roll 15 in stretcher unit 12 and blocks retraction of strips 11. Guide pins 36 at least partially pierce strips 11 to grip strips 11 and guide strips 11 under ultrasonic welder 34. In some embodiments, support roll 32 rotates faster than the last stretcher roll 15 in stretcher unit 12. In some embodiments, support roll 32 has a larger diameter than the last stretcher roll 15 in stretcher unit 12 and rotates at a similar speed to that of the last stretcher roll 15.

Ultrasonic welder 34 is configured to bond strips 11 to non-woven backing web 17 as suggested in FIG. 4. Patterned bonding surface 38 includes a plurality of energy-concentration features 39 as suggested in FIG. 5. Energy-concentration features 39 are configured to concentrate energy from ultrasonic welder 34 to define areas of localized bonding between strips 11 and non-woven backing web 17. In the illustrative embodiment, guide pins 36 are arranged in multiple sections 31 around support roll 32 and along two lanes 42, 44 for guiding separate strips 11a, 11b, respectively, through laminator 14. Each section 31 of guide pins 36 includes leading and trailing rows 43, 45 and side edge columns 47, 49 of guide pins 36 for each lane 42, 44. Sections 31 are distributed around support roll 32 (though only one is shown in FIG. 5). Guide pins 36 are resiliently biased outward and configured to at least partially retract into support roll 32 to minimize damage to guide pins 36 during application of energy from ultrasonic welder 34. In some embodiments, springs bias guide pins 36 outwards. In some embodiments, centrifugal forces from rotation of support roll 32 bias guide pins 36 outward.

Strips 11a, 11b of elastic non-woven 16 are bonded alongside edges of non-woven backing web 17 to form laminate sheet 19 as suggested in FIG. 6. In the illustrative embodiment, absorbent pads 52 are bonded to non-woven backing web 17 between strips 11a, 11b. Laminate sheet 19 can be sectioned into separate diaper chassis 54, as suggested by phantom line 56, for forming diapers, such as a diaper 100 shown in FIG. 9. In some embodiments, non-woven backing web 17 is a single web having a width to receive strips 11a, 11b and absorbent pad 52 thereon. In some embodiments, non-woven backing web 17 includes multiple webs aligned to move in a common direction and each web positioned to receive at least a portion of strips 11a, 11b and absorbent pad 52 thereon. The multiple webs can be spaced apart from one another to underlie strips 11a, 11b and end portions of absorbent pad 52 for example.

Strips 11a, 11b retract when laminate sheet 19 is sectioned into separate diaper chassis 54 to impart elastic qualities to the sections of non-woven backing web 17 where strips 11a, 11b are attached. For example, strips 11a, 11b form at least a portion of a waist band of a diaper, such as in an elastic waist band 102 of diaper 100 shown in FIG. 9, that stretches to accommodate various waist sizes of different wearers. In some embodiments, strips 11a, 11b extend between adjacent absorbent pads 52 as suggested in FIG. 6. In some embodiments, strips 11a, 11b extend part way between adjacent absorbent pads 52 and are spaced apart from absorbent pads 52, such as extending from phantom line 51 to phantom line 53.

In one illustrative embodiment, elastic non-woven ribbons 62, 64 are bonded with non-woven backing web 17 along intersecting sinusoidal patters as suggested in FIG. 7. The bonding patterns of ribbons 62, 64 extend around and intersect between the location of leg holes 66 where material is removed from non-woven backing web 17 during formation of a diaper. Ribbons 62, 64 form leg bands around leg holes 66 of a diaper, such as in an elastic leg band 104 of diaper 100 shown in FIG. 9, that stretches to accommodate various leg sizes of different wearers. Ribbons 62, 64 can be bonded to non-woven backing web 17 using an ultrasonic welder, adhesive material, or any other suitable other bonding method. In some embodiments, ribbons 62, 64 are bonded to non-woven backing web 17 under absorbent pad 52. In some embodiments, portions of ribbons 62, 64 located between leg holes 66, such as those portions that overlap with absorbent pad 52, can be deadened to minimize or eliminate elastic qualities in that location. Deadening may be achieved, for example, by application of heat.

In another illustrative embodiment, elastic non-woven ribbons 61, 63 are bonded with non-woven backing web 17 along leading and trailing edges of absorbent pad 52 as suggested in FIG. 8. Ribbons 61, 63 extend at least partially across non-woven backing web 17, such as between strips 11a, 11b. Ribbons 61, 63 form leg cuffs of a diaper, such as in an elastic leg cuff 106 of diaper 100 shown in FIG. 9, that forms a seal against the legs of a wearer to direct bodily waste toward absorbent pad 52 and block bodily waste from passing through leg holes 66. Ribbons 62, 64 may be bonded to non-woven backing web 17 using an ultrasonic welder, adhesive material, or any other suitable bonding method.

In one example, a lamination system in accordance with the present disclosure is configured to receive the sheet of elastic non-woven material 16 and divide the sheet longitudinally into two continuous strips. The strips are continuously elongated and applied to the non-woven backing web in a continuous and uninterrupted manner to establish the laminate sheet 19. During formation of a diaper, for example, the laminate sheet cut is a cross direction generally perpendicular to a machine direction to form diaper chassis 54. Portions of each diaper chassis may be deadened through the application of heat so that the internal retraction force in those portions is minimized or eliminated. In one example, these deadened portions may correspond with front and rear portions of diaper. Deadening may be accomplished through the application of heat or any other suitable method.

In another example, a lamination system in accordance with the present disclosure is configured to receive the sheet of elastic non-woven material 16 and divide the sheet into strips. Each strip may be cut in a cross direction to form a strip section. Each strip section may be spaced apart longitudinally from other strip sections to form portions of the laminate sheet in which no elastic non-woven is present. In one example, these elastic non-woven free portions may correspond with front and rear portions of a diaper.

One embodiment of a diaper 100 in accordance with the present disclosure is shown in FIG. 9. Diaper 100 is formed using laminate sheet 19 produced by lamination system 10. In the illustrative embodiment, strips 11a, 11b, and the portions of non-woven backing web 17 they are bonded to, are bonded together along seams 101 to define leg holes 66 and a waist opening 103 to form diaper 100. An elastic leg band 104 extends around each leg hole 66 and an elastic waist band 102 extends around waist opening 103. A leg cuff 106 is positioned adjacent to leg hole 66 and alongside absorbent pad 52. In some embodiments, a narrower waist band can be formed, as suggested by phantom line 105, by folding strips 11a, 11b onto themselves to provide a similar retraction force in a smaller area. In some embodiments, graphics 108 are printed on diaper 100. In some embodiments, elastic non-woven material extends from seam 101 on one side of diaper 100 to seam 101 on an opposing side of diaper. To avoid wrinkling of graphics 108, portions of elastic non-woven material in waist band 102 can be deadened to minimize or eliminate elastic qualities in that location.

Another embodiment of a lamination system 210 in accordance with the present disclosure is shown in FIG. 10. Lamination system 210 is similar to lamination system 10 of FIG. 1, and includes a stretcher unit 212 and a laminator 214. A web of elastic non-woven material 216 passes through a cutter 218 of stretcher unit 212 to divide elastic non-woven 216 into strips 211. Strips 211 are carried by a transfer roll 213 of stretcher unit 212 to stretcher rolls 215. Strips 211 pass between stretcher rolls 215 to elongate strips 211 and form an internal retraction force based on the elastic properties of elastic non-woven material 216. The elongated strips 211 pass through laminator 214 to bond with a non-woven backing web 217 to form a laminate sheet 219 (similar to laminate sheet 19 described above). Strips 211 are spaced apart from one another in laminate sheet 219 and impart elastic qualities to laminate sheet 219 where bonded to non-woven backing web 217.

In the illustrative embodiment, laminator 214 includes a support roll 232, an adhesive applicator 234, and a bonding roll 235 as shown in FIG. 10. Adhesive applicator 234 is configured to apply an adhesive material onto non-woven backing web 217 along areas where strips 211 are to be bonded with non-woven backing web 217. Bonding roll 235 and support roll 232 form a nip to force strip 211 and non-woven backing web 217 together against the adhesive material for bonding.

Another embodiment of a lamination system 310 in accordance with the present disclosure is shown in FIG. 11. Lamination system 310 includes a stretcher unit 312 and a laminator 314. A web of elastic non-woven material 316 passes through a cutter 318 of stretcher unit 312 to divide elastic non-woven 316 into strips 311a, 311b. Strips 311a, 311b are carried by transfer rolls 313 to stretcher rolls 372, 374, 376, 378 and guided along separate paths through stretcher unit 312 toward laminator 314. Strips 311a, 311b pass between stretcher rolls 372, 374, 376, 378 to elongate strips 311a, 311b and form an internal retraction force based on the elastic properties of elastic non-woven material 316. The elongated strips 311a, 311b pass through laminator 314 to bond with a non-woven backing web 317 to form a laminate sheet 319 (similar to laminate sheet 19 described above). Strips 311a, 311b are spaced apart from one another in laminate sheet 319 and impart elastic qualities to laminate sheet 319 where bonded to non-woven backing web 317.

In the illustrative embodiment, transfer rolls 313 rotate and engage blades of cutter 318 together to sever elastic non-woven 316 into strips 311a, 311b as suggested in FIG. 11. In some embodiments, an amount of "pre-stretch" elongation can be imparted to elastic non-woven 416 prior to passing through cutter 318. Strips 311b are pulled off of an upper transfer roll 313 by stretcher roll 374. A slip surface 379 of stretcher roll 374 allows strips 311a to be carried by the upper transfer roll 313 to stretcher roll 372. Strips 311a are guided by stretcher roll 372 to support roll 332, and strips 311b are guided by stretcher rolls 374, 376, 378 to support roll 332. Stretcher unit 312 is configured to stretch and align strip 311a, 311b for bonding with non-woven backing web 317 in laminator 314. Laminator 314 includes support roll 332 and an ultrasonic welder 334. Strips 311a, 311b pass through stretcher unit 312 and arrive at laminator 314 at substantially the same time for bonding with non-woven backing web 317 at similar positions along non-woven backing web 317 in a machine direction of lamination system 310. In some embodiments, subsequent strips 311a, 311b created at cutter 318 arrive at different locations along non-woven backing web 317 in the machine direction due to differences in path lengths for each strip 311a, 311b. For example, a strip 311a can arrive simultaneously at laminator 314 with a strip 311b already progressing along stretcher rolls 374, 376, 378 when strip 311a is formed by cutter 318. Strip 311b can be formed one step or multiple steps before strip 311a.

Stretcher unit 312 allows a single incoming or entrance lane 371 of elastic non-woven 316 to be divided into strips 311a, 311b sent along separate lanes 373, 375 to support roll 332 as suggested in FIG. 12. In the illustrative embodiment, transfer rolls 313 and stretcher rolls 372, 374 are aligned along entrance lane 371 and a first strip lane 373. Strips 311a travel along first strip lane 373. Stretcher rolls 376, 378 are frustoconical and arranged to divert strips 311b along a second strip lane 375 spaced apart from first strip lane 373.

Another embodiment of a lamination system 410 in accordance with the present disclosure is shown in FIG. 13. Lamination system 410 includes a stretcher unit 412 and a laminator 414. A web of elastic non-woven material 416 passes through a cutter 418 of stretcher unit 412 to divide elastic non-woven 416 into strips 411a, 411b. In some embodiments, other webs of elastic material, such as netting, apertured or formed films, foams, or sheets for example, are used in place of elastic non-woven web 416. Strips 411a, 411b are carried by transfer rolls 413 of stretcher unit 412 to a stretcher roll 415. Strips 411a, 411b pass between transfer rolls 413 and stretcher roll 415 to elongate strips 411a, 411b and form an internal retraction force based on the elastic properties of elastic non-woven material 416. The elongated strips 411a, 411b pass through laminator 414 to bond with a non-woven backing web 417 to form a laminate sheet 419 (similar to laminate sheet 19 described above). Strips 411 are spaced apart from one another in laminate sheet 419 and impart elastic qualities to laminate sheet 419 where bonded to non-woven backing web 417. In some embodiments, an amount of "pre-stretch" elongation can be imparted to elastic non-woven 416 prior to passing through cutter 418.

In the illustrative embodiment, laminator 414 includes a support roll 432, spaced apart bonding stations 482, 484, and web-steering guides 486 as shown in FIG. 13. Each bonding station 482, 484 includes an adhesive applicator 434 and a bonding roll 435. A first bonding station 482 of laminator 414 is configured to bond strips 411a with non-woven backing web 417.

Adhesive applicator 434 of first bonding station 482 is configured to apply an adhesive material onto non-woven backing web 417 along areas where strips 411a are to be bonded with non-woven backing web 417. Bonding roll 435 of first bonding station 482 and support roll 432 form a nip to force strip 411a and non-woven backing web 417 together against the adhesive material for bonding.

Strips 411b are allowed to bypass first bonding station 482 due to a lack of adhesive applied to coincident portions of non-woven backing web 417 passing through first bonding station 482 with strips 411b as suggested in FIG. 13. Adhesive applicator 434 of second bonding station 484 is configured to apply an adhesive material onto non-woven backing web 417 along areas where strips 411b are to be bonded with non-woven backing web 417. Bonding roll 435 of second bonding station 484 and support roll 432 form a nip to force strip 411b and non-woven backing web 417 together against the adhesive material for bonding. Strips 411b are arranged to pass through second bonding station 484 at substantially the same time as strips 411a for bonding with non-woven backing web 417 at similar positions along non-woven backing web 417 in a machine direction of lamination system 410. In some embodiments, subsequent strips 411a, 411b created at cutter 418 arrive at different locations along non-woven backing web 417 in the machine direction due to differences in path lengths for each strip 411a, 411b. For example, a strip 411b can arrive simultaneously at second bonding station 484 with a strip 411a bonded to non-woven backing web 417 one step or multiple steps before strip 411b.

Laminator 414 allows a single incoming or entrance lane 471 of elastic non-woven strips 411a, 411b to be bonded with non-woven backing web 417 along separate lanes 473, 475 as suggested in FIG. 14. Bonding stations 482, 484 are spaced apart from one another relative to an entrance lane 471 of strips 411a, 411b. First bonding station 482 is arranged relative to support roll 432 to bond strips 411a with non-woven backing web 417 along a first strip lane 473. Web-steering guides 486 guide and align non-woven backing web 417, with strips 411a bonded thereto, with second bonding station 484. Second bonding station 484 is arranged relative to support roll 432 to bond strips 411b with non-woven backing web 417 along a second strip lane 475 to form laminate sheet 419. In some embodiments, an elastic film is used in place of elastic non-woven 416 and vacuum pressure or electrostatic forces are used to hold the film during passage through stretcher unit 412 and laminator 414.

In illustrative embodiments, elastic non-woven material as described herein is useful in replacing individual elastic strands for waist bands, leg bands, and leg cuffs of diapers, or in other textile applications where elastic properties are desired. In some embodiments, elastic non-woven material can be bonded to a non-woven backing web without the use of adhesive materials, unlike individual elastic strands that use significant amounts of adhesive for bonding. In some embodiments, adhesive materials are used for bonding the elastic non-woven material with the non-woven backing web, but less adhesive material is used than for bonding individual elastic strands in the same application. The elastic non-woven material can be folded onto itself to increase retraction force for a given area. Laminate sheets disclosed herein can be formed as "bi-laminates" in contrast to laminate sheets incorporating elastic strands which require a covering material to provide comfortable contact with skin resulting in a "tri-laminate" sheet.

In illustrative embodiments, the elastic non-woven material can be formed from many processes, such as, for example, melt blowing processes, spun bonding processes, hydro entangling processes, and bonded carded web processes.

In illustrative embodiments, the elastic non-woven includes strands having an elastic core and a sheath surrounding the core to provide soft feel and bonding potential with the non-woven backing web. Representative elastomers for the core include but are not limited to the polypropylene elastomer available under the trade designation VISTAMAXX from ExxonMobil (Irving, Tex.), the polyethylene block copolymer elastomer available under the trade designation INFUSE from the Dow Chemical Co., and/or a combination thereof. Other representative non-styrene block copolymers (elastomers or plastomers) suitable for use in accordance with the present disclosure include but are not limited to ethylene copolymers. Representative ethylene copolymers include but are not limited to ethylene vinyl acetates; ethylene octane; ethylene butane; ethylene/propylene copolymer or propylene copolymer elastomers; ethylene/propylene/diene terpolymer elastomers; metallocene polyolefins, such as polyethylene, poly (1-hexane), copolymers of ethylene and 1-hexene, and poly(l-octene); thermoplastic elastomeric polyurethanes, such as that available under the trade designation MORTHANE PE44-203 polyurethane from Morton International, Inc. (Chicago, Ill.) and the trade designation ESTANE 58237 polyurethane from Noveon Corporation, Inc. (Cleveland, Ohio); polyvinyl ethers; poly-a-olefin-based thermoplastic elastomeric materials, such as those represented by the formula —(CH2CHR)x where R is an alkyl group containing from about 2 to about 10 carbon atoms; poly-a-olefins based on metallocene catalysis, such as ENGAGE 8200, ethylene/poly-a-olefin copolymer available from Dow Plastics Co. (Midland, Mich.); polybutadienes; polybutylenes; polyisobutylenes such as VISTANEX NM L-80, available from Exxon Chemical Co.; polyether block amides such as PEBAX available from Elf Atochem North America, Inc. (Philadelphia, Pa.); and/or the like; and combinations thereof.

In illustrative embodiments, thermoplastic elastomeric materials, in particular block copolymers, useful in accordance with the present disclosure for the core of the strands in the elastic non-woven include but are not limited to linear, radial, star, and tapered block copolymers, such as styrene block copolymers. Representative styrene block copolymers for use in accordance with the present disclosure include but are not limited to KRATON or KRATON-based styrene block copolymers available from Kraton Polymers, Inc. (Houston, Tex.), styrene-isoprene block copolymers, styrene-(ethylene-butylene) block copolymers, styrene-(ethylene propylene) block copolymers, styrene-butadiene block copolymers, and/or the like, and combinations thereof. In some embodiments, thermoplastic elastomeric materials in accordance with the present disclosure include polyether esters such as those available under the trade designation HYTREL G3548 from E.I. DuPont de Nemours, and/or polyether block amides such as those available under the trade designation PEBAX from Elf Atochem. Additional thermoplastic materials which may be used in accordance with the present disclosure include but are not limited to polyesters including amorphous polyester, polyamides, fluorinated thermoplastics such as polyvinylidene fluoride; halogenated thermoplastics such as chlorinated polyethylene, polyether-block-amides such as those available under the trade designation PEBAX 5533 from Elf-Atochem, and/or the like, and combinations thereof.

In illustrative embodiments, representative materials for the sheath of the strands in the elastic non-woven include, but are not limited to, polypropylenes, such as polypropylene homopolymers available under the trade designation FORMOLENE from Formosa Plastics Corp.; polypropylene-rich blends, such as a polypropylene homopolymer blended with polyethylene polymers and copolymers available under the trade names ASPUN from the Dow Chemical Co. and ADFLEX Z101H from LyondellBasell Industries; and polyethylene polymers and copolymers.

In illustrative embodiments, the sheath is less than about 50% of the strand cross-section. In some embodiments, the sheath is less than about 25% of the strand cross-section. In some embodiments, the sheath is less than about 20% of the strand cross-section.

The following numbered clauses include embodiments that are contemplated and non-limiting:

Clause 1. A lamination system comprising a stretcher unit and a laminator.

Clause 2. The lamination system of clause 1, any other clause, or combination of clauses, the stretcher including a cutter configured to form strips from a sheet of elastic non-woven material and stretcher rolls located downstream of the cutter.

Clause 3. The lamination system of clause 2, any other clause, or combination of clauses, wherein the laminator is located downstream of the stretcher rolls and configured to receive and bond the strips with a non-woven backing web to form a laminate sheet.

Clause 4. The lamination system of clause 3, any other clause, or combination of clauses, wherein the stretcher rolls are configured to elongate the strips to form an internal retraction force in the strips.

Clause 5. The lamination system of clause 4, any other clause, or combination of clauses, wherein the laminator is configured to bond the strips to the non-woven backing web while the strips are elongated.

Clause 6. The lamination system of clause 5, any other clause, or combination of clauses, wherein the stretcher unit further includes a transfer roll located between the cutter and the stretcher rolls and is configured to transfer the strips from the cutter to the stretcher rolls.

Clause 7. The lamination system of clause 5, any other clause, or combination of clauses, wherein a first of the strips is located in spaced-apart lateral relation to a second of the strips when bonded to the non-woven backing web.

Clause 8. The lamination system of clause 5, any other clause, or combination of clauses, wherein each stretcher roll includes a roller body and a plurality of curved fingers coupled to the roller body to move therewith and each curved finger is arranged to curve outwardly in the direction of rotation of the roller body.

Clause 9. The lamination system of clause 8, any other clause, or combination of clauses, wherein each finger includes a base configured to couple the finger to the roller body and a tip configured to engage a portion of the strips to pull a portion of the strips toward the roller body.

Clause 10. The lamination system of clause 9, any other clause, or combination of clauses, wherein tip of the curved finger pierces the portion of the strips.

Clause 11. The lamination system of clause 8, any other clause, or combination of clauses, wherein a first stretcher roller of the stretcher rolls rotates in a first direction and a second stretcher roller located downstream of the first stretcher roller rotates in a second direction option the first direction.

Clause 12. The lamination system of clause 11, any other clause, or combination of clauses, wherein the first stretcher roller has a first surface speed and the second stretcher roller has a second surface speed greater than the first surface speed.

Clause 13. The lamination system of clause 11, any other clause, or combination of clauses, wherein the first stretcher roller rotates at a first rotational speed and has a first diameter and the second stretcher roller rotates at the first rotation speed and has a second diameter greater than the first diameter.

Clause 14. The lamination system of clause 8, wherein the plurality of curved fingers are arranged along a width of each roller body and in rows spaced-apart circumferentially from one another around each roller body.

Clause 15. The lamination system of clause 5, any other clause, or combination of clauses, wherein the laminator includes a support roll configured to receive the strips and the non-woven backing web and an ultrasonic welder configured to couple the strips to the non-woven backing web using ultrasonic energy.

Clause 16. The lamination system of clause 15, any other clause, or combination of clauses, wherein support roll includes a support-roll body configured to rotate, a plurality of guide pins coupled to the support-roll body to move therewith, and a patterned bonding surface formed on the support roll body configured to cooperate with the ultrasonic welder to focus the ultrasonic energy and bond the strips to the non-woven backing web.

Clause 17. The lamination system of clause 16, any other clause, or combination of clauses, wherein the guide pins are configured to engage and pull the strips off a last stretcher roller included in the stretcher rolls and minimize a loss in elongation of the strips.

Clause 18. The lamination system of clause 17, any other clause, or combination of clauses, wherein the guide pins pierce the strips and guide the strips during ultrasonic welding.

Clause 19. The lamination system of clause 16, any other clause, or combination of clauses, wherein guide pins are arranged in multiple sections around the support-roll body and each section of guide pins includes a leading row, a trailing row spaced apart circumferentially from the leading row, and two edge columns spaced apart laterally from one another and arranged to extend between the leading row and trailing row.

Clause 20. The lamination system of clause 19, any other clause, or combination of clauses, wherein the patterned bonding surface located in area defined between the leading row, the trailing row, and the two edge columns.

Clause 21. The lamination system of clause 12, any other clause, or combination of clauses, wherein the guide pins are movable relative to the support-roll body between an extended position in which the guide pins extend outwardly away from an outer surface of the support-roll body and retracted position in which the guide pins are substantially located at or below the outer surface of the support-roll body and the guide pins are biased toward the extended position.

Clause 22. The lamination system of clause 5, any other clause, or combination of clauses, wherein each strip comprises a plurality of strip sections and each strip section is spaced apart from a neighboring strip section once the strip has been coupled to the non-woven backing web.

Clause 23. The lamination system of clause 5, any other clause, or combination of clauses, wherein each strip is coupled to the non-woven backing web continuously without interruption.

Clause 24. The lamination system of clause 23, any other clause, or combination of clauses, wherein portions of each strip are deadened to cause the internal retraction force in the portions to be minimized.

Clause 25. The lamination system of clause 23, any other clause, or combination of clauses, further comprising a heater configured to apply heat selectively to the portions to deaden the portions.

Clause 26. The lamination system of clause 5, any other clause, or combination of clauses, wherein the laminator includes a support roll configured to receive the strips and the non-woven backing web, an adhesive applicator configured to apply adhesive to the non-woven backing web, and a bonding roll configured to force the strips, the adhesive, and the non-woven backing web together to form a laminate sheet.

Clause 27. The lamination system of clause 5, any other clause, or combination of clauses, wherein stretcher rolls includes a first stretcher roller including a grip surface configured to grip a first strip of the strips and transfer the first strip to the first stretcher roller and a slip surface configured to allow a second subsequent strip of the strips to move relative to the first stretcher roller to a second stretcher roller included in the stretcher rolls which engages the second strip to transfer the second strip to the second stretcher roller.

Clause 28. The lamination system of clause 27, any other clause, or combination of clauses, wherein the stretcher rolls includes a first transfer roll located upstream of the first and second stretcher rollers and a second transfer roller located between the first transfer roller and the first and second stretcher rollers and the cutter is located between the first and second transfer rollers.

Clause 29. The lamination system of clause 28, any other clause, or combination of clauses, wherein the cutter cuts the sheet in a cross direction which is generally perpendicular to a machine direction.

Clause 30. The lamination system of clause 27, any other clause, or combination of clauses, wherein the stretcher rolls move the first strip laterally away from the second strip to cause the first and second strips to be located in spaced-apart lateral relation to one another when the strips are bonded to the non-woven backing layer by the laminator.

Clause 31. The lamination system of clause 30, any other clause, or combination of clauses, wherein the stretcher rolls are frustoconical.

Clause 32. The lamination system of claim 5, any other clause, or combination of clauses, wherein the stretcher unit includes a single entrance lane along which the sheet moves and two output lanes along which strips are provided to the laminator.

Clause 33. The lamination system of clause 5, any other clause, or combination of clauses, wherein each strip comprises a plurality of strip sections and each strip section is spaced apart from a neighboring strip section once the strip has been coupled to the non-woven backing web.

Clause 34. The lamination system of clause 33, any other clause, or combination of clauses, wherein the laminator includes a support roll configured to receive the strip sections and the non-woven backing web, a first adhesive applicator configured to apply adhesive to the non-woven backing web in a first area, a first bonding roll configured to force a first strip section included in the strip sections, the adhesive in the first area, and the non-woven backing web together to form a first lane.

Clause 35. The lamination system of clause 34, wherein the lamination includes a second adhesive applicator located downstream of the first adhesive applicator and configured to apply adhesive to the non-woven backing web in a second area, a second bonding roll configured to force a second subsequent strip section included in the strip sections, the adhesive in the second area, and non-woven backing web together to form a second lane spaced-apart laterally from the first lane so that the laminate sheet is established.

Clause 36. The lamination system of clause 35, any other clause, or combination of clauses, wherein the laminator further includes a web guide located between the first adhesive applicator and the second adhesive applicator and configured to move the non-woven backing web lateral relative to the support roll to cause the first strip to be located in spaced-apart relation to the second strip.

Clause 37. The lamination system of clause 36, any other clause, or combination of clauses, wherein the first adhesive applicator applies adhesive to the first area and does not apply adhesive to another area directly behind the first area as the non-woven backing web moves downstream.

The invention claimed is:

1. A lamination system comprising:
   a stretcher unit including a cutter and one or more stretcher rolls located downstream of the cutter; wherein the cutter separates a web of elastic material into a plurality of strips;
   a means for placing each of the plurality of strips into a spaced-apart lateral position relative to one another; and
   a laminator configured to receive and bond the plurality of strips with a non-woven backing web to form a laminate sheet;
   wherein the one or more stretcher rolls are configured to elongate the web of elastic material or the plurality of strips to form an internal retraction force therein;
   wherein the laminator is configured to bond the plurality of strips to the non-woven backing web while the plurality of strips are elongated;
   wherein the laminator includes a support roll configured to receive the plurality of strips and the non-woven backing web, and an ultrasonic welder configured to couple the plurality of strips to the non-woven backing web using ultrasonic energy;
   wherein the support roll includes a support-roll body configured to rotate and a bonding surface formed on the support-roll body configured to cooperate with the ultrasonic welder to focus the ultrasonic energy and bond the plurality of strips to the non-woven backing web.

2. The lamination system of claim 1, wherein the web of elastic material is a non-woven, a film, a sheet, a netting, or combinations thereof.

3. The lamination system of claim 2, wherein the film is a perforated film.

4. The lamination system of claim 1, wherein the bonding surface is patterned.

5. The lamination system of claim 4, wherein the bonding surface is patterned with a sinusoidal pattern.

6. The lamination system of claim 5, wherein the sinusoidal pattern is an intersecting sinusoidal pattern.

7. The lamination system of claim 1, wherein the means for placing each of the plurality of strips into a spaced-apart lateral position relative to one another is located upstream from the stretcher.

8. The lamination system of claim 1, wherein the means for placing each of the plurality of strips into a spaced-apart lateral position relative to one another is located downstream from the stretcher.

9. The lamination system of claim 1, wherein one or more of the stretcher rolls comprises a roller body and a plurality of curved fingers coupled to the roller body to move therewith and each curved finger is arranged to curve outwardly in the direction of rotation of the roller body.

10. The lamination system of claim 1, wherein vacuum pressure is applied to one or both of the stretcher unit or the laminator.

11. The lamination system of claim 1, wherein the support roll further includes a plurality of guide pins coupled to the support-roll body to move therewith.

12. The lamination system of claim 11, wherein the support roll includes a support-roll body configured to rotate, a plurality of guide pins coupled to the support-roll body to move therewith, and a bonding surface formed on the support-roll body configured to cooperate with the ultrasonic welder to focus the ultrasonic energy and bond the plurality of strips to the non-woven backing web.

13. The lamination system of claim 11, wherein the web of elastic material is a non-woven, a film, a perforated film, a sheet, a netting, or combinations thereof.

14. The lamination system of claim 11, wherein the means for placing each of the plurality of strips into a spaced-apart lateral position relative to one another is located upstream from the stretcher.

15. The lamination system of claim 11, wherein the means for placing each of the plurality of strips into a spaced-apart lateral position relative to one another is located downstream from the stretcher.

16. The lamination system of claim 11, wherein vacuum pressure is applied to one or both of the stretcher unit and the laminator.

17. A lamination system comprising:
   a stretcher unit including a cutter and one or more stretcher rolls located downstream of the cutter; wherein the cutter separates a web of elastic material into a plurality of strips;
   a means for placing each of the plurality of strips into a spaced-apart lateral position relative to one another; and
   a laminator located downstream of the one or more stretcher rolls and configured to receive and bond the plurality of strips with a non-woven backing web to form a laminate sheet;
   wherein the one or more stretcher rolls are configured to elongate the web of elastic material or the plurality of strips to form an internal retraction force therein;
   wherein the laminator is configured to bond the plurality of strips to the non-woven backing web while the plurality of strips are elongated;
   wherein the laminator includes a support roll configured to receive the plurality of strips and the non-woven backing web, and an ultrasonic welder configured to couple the plurality of strips to the non-woven backing web using ultrasonic energy; and,
   wherein one or more of the one or more stretcher rolls comprises a roller body and a plurality of curved fingers coupled to the roller body to move therewith and each curved finger is arranged to curve outwardly in the direction of rotation of the roller body.

18. The lamination system of claim 17, wherein the bonding surface is patterned.

19. The lamination system of claim 18, wherein the bonding surface is patterned with a sinusoidal pattern.

20. A lamination system comprising:
   a stretcher unit including a cutter and one or more stretcher rolls wherein the cutter separates a web of elastic material into a plurality of strips;
   a means for placing each of the plurality of strips into a spaced-apart lateral position relative to one another; and
   a laminator configured to receive and bond the plurality of strips with a non-woven backing web to form a laminate sheet;
   wherein the one or more stretcher rolls are configured to elongate the web of elastic material or the plurality of strips to form an internal retraction force therein;
   wherein the laminator is configured to bond the plurality of strips to the non-woven backing web while the plurality of strips are elongated;
   wherein the laminator includes a support roll configured to receive the plurality of strips and the non-woven backing web, and an ultrasonic welder configured to couple the plurality of strips to the non-woven backing web using ultrasonic energy;

wherein the support roll includes a support-roll body configured to rotate and a bonding surface formed on the support-roll body configured to cooperate with the ultrasonic welder to focus the ultrasonic energy and bond the strips to the non-woven backing web.

* * * * *